US008389673B2

(12) United States Patent
Timberlake et al.

(10) Patent No.: US 8,389,673 B2
(45) Date of Patent: Mar. 5, 2013

(54) ARYL ETHER OLIGOMERS AND PROCESS FOR MAKING ARYL ETHER OLIGOMERS

(75) Inventors: Larry D. Timberlake, West Lafayette, IN (US); Julia E. Holland, Indianapolis, IN (US)

(73) Assignee: Chemtura Corporation, Middlebury, CT (US)

( * ) Notice: Subject to any disclaimer, the term of this patent is extended or adjusted under 35 U.S.C. 154(b) by 489 days.

(21) Appl. No.: 12/533,558

(22) Filed: Jul. 31, 2009

(65) Prior Publication Data

US 2011/0024703 A1    Feb. 3, 2011

(51) Int. Cl.
*C08F 6/06* (2006.01)
*C08F 6/10* (2006.01)
*C08G 65/38* (2006.01)
*C08G 65/40* (2006.01)
*C08G 65/46* (2006.01)

(52) U.S. Cl. ........ 528/486; 528/205; 528/219; 528/485; 528/489; 528/495; 528/501; 528/502 R; 528/503

(58) Field of Classification Search .................. 252/609; 528/485, 486, 489, 495, 501, 502 R, 503, 528/205, 219
See application file for complete search history.

(56) References Cited

U.S. PATENT DOCUMENTS

| | | | |
|---|---|---|---|
| 3,228,910 | A | 1/1966 | Stamatoff et al. |
| 3,332,909 | A | 7/1967 | Farnham et al. |
| 3,760,003 | A | 9/1973 | Asadorian et al. |
| 4,258,175 | A | 3/1981 | Chen et al. |
| 4,550,210 | A | 10/1985 | Hedberg et al. |
| 4,870,153 | A | 9/1989 | Matzner et al. |
| 5,530,044 | A | 6/1996 | Mack et al. |
| 6,756,470 | B2 | 6/2004 | Keller et al. |
| 6,891,014 | B2 | 5/2005 | Keller et al. |
| 2002/0161174 | A1 | 10/2002 | Sasaki et al. |
| 2008/0269416 | A1 | 10/2008 | Timberlake et al. |

FOREIGN PATENT DOCUMENTS

| | | |
|---|---|---|
| FR | 1301174 | 8/1962 |
| GB | 1415945 | 12/1975 |
| JP | 63281425 | 11/1988 |
| WO | 2008/134294 | 11/2008 |
| WO | 2008/156928 | 12/2008 |

OTHER PUBLICATIONS

Dhanesar et al—Synthesis and Stationary Phase Properties of Bromo Phenyl Ethers, Journal of Chromatography, 267 (1983), pp. 293-301.
Ley, S. V. and Thomas, A. W.—Modern Synthetic Methods for Copper-Mediated C(aryl)-O, C(aryl)-N, and C(aryl)-S Bond Formation; Angew. Chem. Int. Ed. 2003, 42, 5400-5449.
Sawyer, J. S.—Recent Advances in Diaryl ether Synthesis; Tetrahedron, 2000, 56, 5045-5065.
Lindley, James—Copper Assisted Nucleophilic Substitution of Aryl Halogen; Tetrahedron, 1984, 40(9), 1433-1456.
Frlan, R. and Kikelj, D.—Recent Progress in Diaryl Ether Synthesis; Synthesis, 2006, 14, 2271-2285.
Ungnade, H. E.—the Chemistry of the Diaryl Ethers; Chemical Reviews, 1946, 38, 405-414; citing Staudinger, H. and Staiger, F. Ann. 1935, 517, 67.
Hammann, W. C. and Schisla, R. M.—Synthesis of Seven New Polyphenyl Ethers; J. Chem. Eng. Data 1970, 15(2), 352-355.
Dort, et al, Poly-p-Phenylene Oxide; European Polymer Journal, 1968, 4, 275-287.
Jurek, M. J. and McGrath, J. E.—The Synthesis of Poly (Arylene ethers) via the Ullmann Condensation Reaction; Polymer Preprints 1987, 28(1), 180-1.
Dominguez, D. D. and Keller, T. M.—Low-melting Phthalonitrile Oligomers: Preparation, Polymerization and Polymer Properties; High Performance Polymers 2006, 18, 283-304.
Laskoski, M.; Dominguez, D. D. and Keller, T. M.—Oligomeric Cyanate Ester Resins: Application of a Modified Ullmann Synthesis in the Preparation of Thermosetting Polymers; J. Polym. Sci. A: Polym. Chem. 2006 44, 4559-4565.
Laskoski, M.; Dominguez, D. D.and Keller, T. M.—Synthesis and Properties of a Liquid Oligomeric Cyanate Ester Resin Polymer 2006, 47, 3727-3733.
Marcoux, J. F.; Doye, S. and Buchwald, S. L.—A General Copper-Catalyzed Synthesis of Diaryl Ethers; J. Am. Chem. Soc. 1997, 119, 10539.
Lindley, P. M.; Picklesimer, L. G.; Evans, B.; Arnold, F. E. and Kane, J. J. Arylether Sulfone Oligomers with Acetylene Termination from the Ullmann Ether Reaction, in ACS Symp. Ser. 282, Ch. 3, 1985, 31-42.
Hedberg, F. L.; Unroe, M. R.; Lindley, P. M. and Hunsaker, M. E.—A General Preparation of Tailored-length Acetylene Terminated Resins from Low Cost Bisphenols; Wright Patterson Air Force Base Technical Report AFWAL—TR-85-4041, 1985.
Lee, J. I.; Kwon, L. Y.; Kim, J.-H.; Choi, K.-Y. and Suh, D. H.—Synthesis of New Poly(aryl ether)s with Pendent Benzoxazole via Ullmann Ether Reaction; Die Angewandte Makromolekulare Chemie 1998, 254, 27-32, Lee, et al.
Chang, J. W. W. et al—Copper-catalyzed Ullmann Coupling Under ligand- and additive-free Conditions. Part 1: O-Arylation of phenols with aryl halides; Tet. Lett. 2008, 49, 2018-2022.
Williams, A. L.; Kinney, R. E. and Bridger, R. F.—Solvent-Assisted Ullmann Ether Synthesis. Reactions of Dihydric Phenols; J. Org. Chem. 1967, 32, 2501-2505.
Goodbrand, H. B. and Hu, N.-X.—Ligand-Accelerated Catalysts of the Ullmann Condensation: Application to Hole Conducting Triarylamines; J. Org. Chem. 1999, 64, 670-674.
Rao, H. et al—A Versatile and Efficient Ligand for Copper-Catalyzed Formation of C-N, C-O, and P-C Bonds: Pyrrolidine-2-Phosphonic Acid Phenyl Monoester; Chem. Eur. J. 2006, 12, 3636-3646; Wang, B.-A. et al Chinese J. Chem. 2006, 24, 1062-1065.

(Continued)

*Primary Examiner* — Duc Truong
(74) *Attorney, Agent, or Firm* — Joseph Suhadolnik

(57) ABSTRACT

An aryl composition includes aryl ether oligomers. These compositions may be prepared by reaction of one or more dihalobenzenes with one or more dihydroxybenzenes by an Ullman ether reaction. The oligomers may have two or more benzene rings and include terminal halogen, e.g., bromine (Br), or hydroxyl (OH) groups. These oligomers may be brominated to form flame retardant compositions for thermoplastic polymers.

13 Claims, No Drawings

OTHER PUBLICATIONS

Ma, D. And Cai, Q.—N,N-Dimethyl Glycine-Promoted Ullmann Coupling Reaction of Phenols and Aryl Halides; Org. Lett. 2003, 5, 3799.

Cristau, H.-J. et al—A General and Mild Ullmann-Type Synthesis of Diaryl Athers; Org. Lett. 2004, 6(6), 913-916.

Ghosh, R. And Samuelson, A. G.—Copper Promoted Synthesis of Diaryl Ethers; New J. Chem. 2004, 28, 1390-1393.

Weingarten, H.J—Mechanism of the Ullmann Condensation; Org. Chem.1964, 29, 3624-3626.

Wang, B.-A. et al—Copper(II) and 2,2-Biimidazolyl-promoted Ullmann Coupling Reaction of Phenols and Aryl Iodides; Chinese J. Chem. 2006, 24, 1062-1065.

Timberlake et al.—Flame Retardant Halogenated Aryl Ether Oligomer Compositions and Their Production—U.S. Appl. No. 12/533,602, filed Jul. 31, 2009.

ARYL ETHER OLIGOMERS AND PROCESS FOR MAKING ARYL ETHER OLIGOMERS

FIELD

This invention relates to aryl ether oligomers and a process for making aryl ether oligomers.

BACKGROUND

Decabromodiphenyl oxide (deca) and decabromodiphenylethane (deca-DPE) are commercially available materials widely used to flame retard various polymer resin systems. The structure of these materials is as follows:

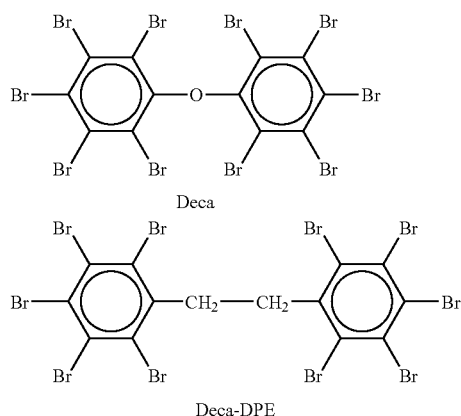

One of the advantages of using deca and deca-DPE in polymer resins that are difficult to flame retard, such as high-impact polystyrene (HIPS) and polyolefins, is that the materials have a very high (82-83%) bromine content. This allows a lower load level in the overall formulation, which in turn serves to minimize any negative effects of the flame retardant on the mechanical properties of the polymer.

Despite the commercial success of deca, there remains significant interest in developing alternative halogenated flame retardant materials that are equally or more efficient, not only because of economic pressures but also because they may allow lower flame retardant loadings, which in turn may impart improved performance properties. Improved properties, such as non-blooming formulations, or better mechanical properties can potentially be met by producing polymeric or oligomeric flame retardant compounds. These types of materials would become entangled in the base resin polymer matrix, depending on the compatibility, and hence should show fewer tendencies to bloom.

There are a number of commercially available flame retardant materials that can be considered oligomers or polymers of halogenated monomers. Examples of these monomers include tetrabromobisphenol A (TBBPA) and dibromostyrene (DBS), which have the following structures:

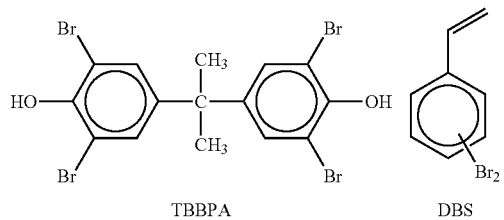

Commercially, TBBPA and DBS are typically not used in their monomeric form, but are converted into an oligomeric or polymeric species. One class of oligomers is the brominated carbonate oligomers based on TBBPA. These are commercially available from Chemtura Corporation (examples include Great Lakes BC-52™, Great Lakes BC-52HP™, and Great Lakes BC-58™) and by Teijin Chemical (FireGuard 7500 and FireGuard 8500). These products are used primarily as flame retardants for polycarbonate and polyesters.

Brominated epoxy oligomers, based on condensation of TBBPA and epichlorohydrin, are commercially available and sold by Dainippon Ink and Chemicals under the Epiclon® series, and also by ICL Industrial Products (examples are F-2016 and F-2100) and other suppliers. The brominated epoxy oligomers find use as flame retardants for various thermoplastics both alone and in blends with other flame retardants.

Another class of brominated polymeric flame retardants based on TBBPA is exemplified by Teijin FG-3000, a copolymer of TBBPA and 1,2-dibromoethane. This aralkyl ether finds use in ABS and other styrenic polymers. Alternative end-groups, such as aryl or methoxy, on this polymer are also known as exemplified by materials described in U.S. Pat. No. 4,258,175 and U.S. Pat. No. 5,530,044. The non-reactive end-groups are claimed to improve the thermal stability of the flame retardant.

TBBPA is also converted into many other different types of epoxy resin copolymer oligomers by chain-extension reactions with other difunctional epoxy resin compounds, for example, by reaction with the diglycidylether of bisphenol A. Typical examples of these types of epoxy resin products are D.E.R.™ 539 by the Dow Chemical Company, or Epon™ 828 by Hexion Corporation. These products are used mainly in the manufacture of printed circuit boards.

DBS is made for captive use by Chemtura Corporation and is sold as several different polymeric species (Great Lakes PDBS-80™, Great Lakes PBS-64™, and Firemaster CP44-HF™) to make poly(bromostyrene) type flame retardants. These materials represent homopolymers or copolymers. Additionally, similar brominated polystyrene type flame retardants are commercially available from Albemarle Chemical Corporation (Saytex® HP-3010, Saytex® HP-7010, and PyroChek 68PB). All these polymeric products are used to flame retard thermoplastics such as polyamides and polyesters.

Unfortunately, one of the key drawbacks of the existing brominated polymer materials is their relatively low bromine content, which makes them less efficient as a flame retardant and consequently typically has a negative effect on the desirable physical properties of the flame retardant formulations containing them, such as impact strength. For example, whereas deca and deca-DPE contain 82-83% bromine, oligomers or polymers based on the brominated monomers mentioned above generally have a bromine content in the range of 52% -68%, depending on the material. This therefore typically requires a flame retardant loading level in a polymer formulation significantly higher than that required for deca, often resulting in inferior mechanical properties for the formulation.

Other considerations also influence the impact the flame retardant has on the final properties of the formulated resin. These considerations include the flame retardant thermal stability and the compatibility with the host resin. In situations where these other considerations are relatively constant, the bromine content, and hence flame retardant load level, has a major influence on the properties of the overall formulation.

To address the need for flame retardant materials that to not detract from the mechanical properties of the target resin, we have now developed a family of materials that can be classified as halogenated, and particularly brominated, aryl ether oligomers. In particular, we have found that the use of these halogenated aryl ether oligomers results in superior mechanical properties in resins such as HIPS and polyolefins and that the materials also provide excellent properties in engineering thermoplastics such as polyamides and polyesters. The aryl ether oligomers can be halogenated to a higher level than the oligomers and polymers that are commercially available today, which should have a positive effect on their mechanical property performance. It is also found that these aryl aryl ether oligomers, even at lower levels of halogenation, give formulations with acceptable mechanical properties.

Japanese Unexamined Patent Application Publication 2-129,137 discloses flame retardant polymer compositions in which the polymer is compounded a with halogenated bis(4-phenoxyphenyl)ether shown as follows:

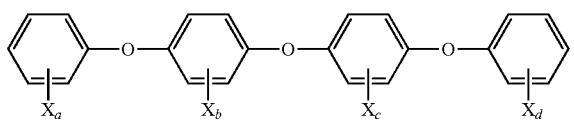

in which X is a halogen atom, a and d are numbers in the range of 1-5, and b and c are numbers in the range of 1-4. However, the flame retardant is produced by brominating the bis(4-phenoxyphenyl)ether as a discrete compound and not an oligomeric material obtained by polymerizing an aryl ether monomer. In contrast, employing a material having an oligomeric distribution is believed to improve its performance properties as a flame retardant.

U.S. Pat. No. 3,760,003 discloses halogenated polyphenyl ether flame retardants having the general formula:

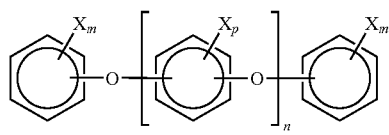

wherein each X is independently Cl or Br, each m is independently an integer of 0 to 5, each p is independently an integer of 0 to 4, n is an integer of 2 to 4, and 50% or more by weight of the compound is halogen. The ether precursors again appear to be discrete non-polymeric materials and are halogenated by reaction with bromine in the presence of iron powder as a catalyst and optionally methylene bromide. After the reaction is complete, the excess bromine is flash vaporized, leaving behind the desired solid product.

In an article entitled "Synthesis and Stationary Phase Properties of Bromo Phenyl Ethers, *Journal of Chromatography*, 267 (1983), pages 293-301, Dhanesar et al disclose a process for the site-specific bromination of phenyl ethers containing from 2 to 7 benzene rings. Again the ethers appear to be discrete compounds with no oligomeric distribution and, although the products are said to be useful in the separation of organic compounds, no reference is given to their possible use as flame retardants.

United States Patent Application Publication Number US 2008/0269416, which corresponds to International Publication Number WO 2008/134294, describes a halogenated aryl ether oligomer that comprises the following repeating monomeric units:

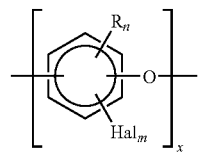

wherein R is hydrogen or alkyl, especially $C_1$ to $C_4$ alkyl, Hal is halogen, normally bromine, m is at least 1, n is 0 to 3 and x is at least 2, such as 3 to 100,000, for example 5 to 20. These oligomers may be prepared by brominating an intermediate oligomer composition. In Example 8 of US 2008/026416 and WO 2008/134294, the intermediate oligomer composition is prepared by an Ullmann ether reaction of resorcinol and 1,4-dibromobenzene in a 1:1 molar ratio and in the presence of a cuprous iodide (i.e. CuI) catalyst. In Example 9 of US 2008/0269416 and WO 2008/134294, the intermediate oligomer composition is prepared by oligomerizing 3-bromophenol. In Example 10 of US 2008/0269416 and WO 2008/134294, the intermediate oligomer composition is prepared by oligomerizing 4-bromophenol.

In our co-pending U.S. Provisional Patent Application No. 61/139,282, filed Dec. 19, 2008, we have described a flame retardant blend comprising at least first and second halogenated phenyl ethers having the general formula:

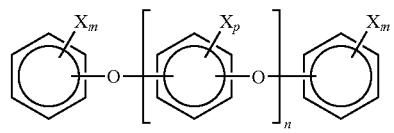

wherein each X is independently Cl or Br, each m is independently an integer of 1 to 5, each p is independently an integer of 1 to 4, n is an integer of 1 to 5 and wherein the values of n for the first and second ethers are different. Bromination is conveniently effected by adding bromine to a solution of the blended ether precursors in dichloromethane also containing an aluminum chloride catalyst. The reaction temperature is kept at 30° C. and the HBr off-gas is captured in a water trap. After the HBr evolution subsides, the material is worked up to give the product as an off-white solid.

WO2008/156928 discloses optoelectronic polymer compositions made from brominated polyarylethers having pendant carbazolyl groups. Useful polyarylethers are made by nucleophilic displacement condensation reactions between bisphenols and dihalogenated monomers. The resultant polyarylethers are then subjected to electrophilic aromatic substitution with bromine followed by nucleophilic aromatic substitution with a carbazole compound. Bromine substitution is typically effected by adding bromine dropwise to a solution of the ether in chloroform followed by precipitation with methanol.

The synthesis of aryl ethers via the Ullmann ether reaction has been reviewed quite extensively and has been known for over 100 years. Articles on this subject include Ley, S. V. and Thomas, A. W. *Angew. Chem. Int. Ed.* 2003, 42, 5400-5449; Sawyer, J. S. *Tetrahedron*, 2000, 56, 5045-5065; Lindley, James *Tetrahedron*, 1984, 40(9), 1433-1456; and Frlan, R. and Kikelj, D. *Synthesis*, 2006, 14, 2271-2285. The vast majority of information on this subject deals with making diaryl ethers from aryl halides and phenoxides and only a very small portion covers any research on making polymers or oligomers using this technology. In a 1945 review by Ungnade, H. E. *Chemical Reviews*, 1946, 38, 405-414; citing Staudinger, H. and Staiger, F. *Ann*. 1935, 517, 67, it was disclosed that small-chain oligomer type aryl ethers were made from a stepwise build-up using the appropriate aryl halide and phenoxide. In this case, for example, the authors used the reaction of a 4-ring α,ω-dibromo aryl ether with potassium phenoxide to make a six-ring aryl ether species. Other small-chain oligomers made in this fashion have also been reported by Hammann, W. C. and Schisla, R. M. *J. Chem. Eng. Data* 1970, 15(2), 352-355.

The preparation of polymers or oligomers of aryl ethers has generally been done by either homopolymerization of a halophenol, or co-polymerization of an aryldihalide with an aryldiphenol. One of the earlier works done on the polymerization of bromophenol using Ullmann chemistry was by Stamatoff (DuPont), as described U.S. Pat. No. 3,228,910 and FR 1,301,174. In these patents, it was mentioned that the reaction was conducted in an inert solvent in which sodium phenate is soluble. In this case they used such solvents as dimethylacetamide, m-dimethoxy benzene, or nitrobenzene. The catalyst was a cuprous chloride—pyridine complex. In 1968, van Dort, et al, as described in van Dort, H. M., et al *European Polymer Journal*, 1968, 4, 275-287, made a polymer from para-bromophenol under Ullmann conditions by reacting the sodium salt of the phenol using a cuprous chloride—pyridine catalyst complex in dimethoxybenzene at temperatures up to 200° C. Another polymerization synthesis using p-bromophenol was from Jurek and McGrath, as described in Jurek, M. J. and McGrath, J. E. *Polymer Preprints* 1987, 28(1), 180-1. In this case they used a cuprous chloride—quinoline complex as the catalyst with benzophenone as the solvent and used reaction temperatures up to 210° C. They also used an azeotrope solvent, such as toluene, to remove the water formed during the reaction of bromophenol with base. Once the phenate was formed and the water was removed, the toluene was stripped from the reaction to allow the polymerization to proceed at the high temperatures required.

Access to aryl ether oligomers having meta-substitution by this route is not as easy, since the meta isomer for the bromphenol starting material is less available than the para isomer of bromophenol. The alternative approach of embodiments described herein can lead to meta substitution more easily, since, in the case of resorcinol, that material is already meta-substituted.

A series of papers appear from Keller, et al, regarding the formation of aryl ether oligomers by reactions of aryldihalides with aryldiphenols. These papers include Dominguez, D. D. and Keller, T. M. *High Performance Polymers* 2006, 18, 283-304; Laskoski, M.; Dominguez, D. D. and Keller, T. M. *J. Polym. Sci. A: Polym. Chem.* 2006, 44, 4559-4565; and Laskoski, M.; Dominguez, D. D. and Keller, T. M. *Polymer* 2006, 47, 3727-3733. The main focus of these publications is to make thermosetting cyanate ester or phthalonitrile based resins in which the reactive monomer groups are separated by aryl ether spacer groups. In the aryl ether synthesis, they use a process in which a diphenol (such as resorcinol) is reacted with an aryldihalide (such as 1,3-dibromobenzene) in a solvent system similar to that described above using toluene and DMF, where the toluene is used to azeotrope any water formed in the reaction. They use either cuprous iodide—1,10-phenanthroline or a triphenylphosphine—copper bromide complex as the catalyst system with potassium carbonate as the base. In all cases, the reactions were run with excess of the diphenol, so the oligomer that is formed would have reactive end groups for the next step in the synthesis. They showed that in this solvent system, they could use the potassium carbonate base instead of the more expensive cesium carbonate system developed by Buchwald and co-workers 10 years earlier, as described in Marcoux, J. F.; Doye, S. and Buchwald, S. L. *J. Am. Chem. Soc.* 1997, 119, 10539. One of the drawbacks in using a carbonate base for the reaction is that the excess solid base that is used would need to be dealt with in some fashion during product workup. Depending on the reaction concentration, the solid bases may also create problems in handling the resulting thick slurry. Two patents to Keller, et al, i.e. U.S. Pat. No. 6,891,014 B2 and U.S. Pat. No. 6,756,470 B2, also describe reactions run with an excess of diphenol to form oligomers with reactive hydroxyl end groups as intermediates for the preparation of desired oligomeric hydroxyl arylether phthalonitrile end products. However, these patents also mention that diphenols may be reacted with dihalobenzene in a 1:1 molar ratio or with the dihalobenzene in molar excess of the diphenol. In particular, it is stated at column 6, lines 16-20 of U.S. Pat. No. 6,891,014 B2 and at column 6, lines 32-35 of U.S. Pat. No. 6,756,470 B2 that a 2:1 molar ratio of m-diiodobenzene and hydroquinone would react to form oligomers, where the average chain has three benzene rings.

Other examples are found in the literature where aryl ether oligomers are prepared from reaction of diphenolics with aryldihalides. In a report by Lindley, et al, in 1985, i.e. Lindley, P. M.; Picklesimer, L. G.; Evans, B.; Arnold, F. E. and Kane, J. J. *Arylether Sulfone Oligomers with Acetylene Termination from the Ullmann Ether Reaction*, in ACS Symp. Ser. 282, Ch. 3, 1985, 31-42, potassium carbonate was used either in pyridine with cuprous iodide or in collidine with cuprous oxide. It was mentioned that formation of oligomers with more than three benzene rings could be minimized by using a large excess of the aryldibromide. Lindley further reports that the chain length for the formation of the aryl ether oligomers can be controlled by adjustment of the reaction stoichiometry. See Hedberg, F. L.; Unroe, M. R.; Lindley, P. M. and Hunsaker, M. E. *Wright Patterson Air Force Base Technical Report AFWAL-TR-85-4041*, 1985. Oligomers were obtained using resorcinol and 1,3-dibromobenzene at 1:10 and 1:2 mol ratios. In the single reaction where the molar ratio of resorcinol to 1,3-dibromobenzene was 1:2, the percent yield was reported as 49 wt %.

A U.S. patent by Famham, et al, i.e. U.S. Pat. No. 3,332,909, discloses that polyarylene polyethers can be made from reaction of a dihydric phenol with a dibromobenzenoid compound. They mention that an alkali metal hydroxide can be used to form the metal salt of the dihydric phenol and that the water formed in the reaction can be removed with the aid of an azeotropic solvent, such as toluene, with the main solvent being benzophenone and the catalyst being a cuprous salt, such as cuprous chloride—pyridine complex. In a 1989 patent, i.e. U.S. Pat. No. 4,870,153, Matzner, et al, discloses synthesis of poly(aryl ether) polymers by a similar approach using a cuprous halide catalyst as a pyridine complex in a solvent like benzophenone with reaction temperatures in the 180-220° C. range. Both authors also employ adding a monofunctional compound, such as bromobenzene toward the end of the reaction to endcap any residual phenolic species and also mention that the stoichiometry for the two reactants needs to be within 5% of 1:1, or the molecular weight would be significantly reduced.

In a 1998 paper, i.e. Lee, J. I.; Kwon, L. Y.; Kim, J.-H.; Choi, K.-Y. and Suh, D. H. *Die Angewandte Makromolekulare Chemie* 1998, 254, 27-32, Lee, et al discusses polymer formation using a CuCl-pyridine complex in N-methyl-2-pyrrolidone (NMP) with either potassium carbonate or NaOH as the base and using toluene as the azeotropic solvent for water removal.

The approaches discussed above require reaction times of near 24 hr to complete the reaction or reaction temperatures near 200° C. It would, therefore, be desirable to improve the catalyst system or solvent system that is used.

It would appear that improvements in copper catalyst systems for the Ullmann ether reaction have been occurring more frequently in the last 20 years in the reactions of various monohalo benzenes with certain phenols to make simple aryl ethers. The catalysts used in the vast majority of reports are cuprous salts. In a mechanistic paper, i.e. Weingarten, H. *J. Org. Chem.* 1964, 29, 3624-3626, involving such catalysts, it was mentioned that cupric species get converted into cuprous species during the reaction and that cuprous is the active catalytic species. A Great Britain patent, i.e. Wedemeyer, K. and Adolphen, G. GB 1,415,945 (1975), discussed using cupric oxide, cuprous oxide, cupric bromide, or cuprous bromide, etc., in the synthesis of small aryl ether molecules by reaction of a chlorophenol with excess dichlorobenzene. They needed to use a deficit of base to achieve reasonable yields in the reaction and needed about 30% of free phenol to be present to achieve the maximum 70-75% yield.

Advantages of using a cupric salt vs. cuprous in the Ullmann reaction of aryl ether oligomers or polymers do not appear to be described in the published literature. The molecular weights of cupric oxide, cuprous oxide and cuprous iodide are 79.55, 143.1, and 190.5 g/mol, respectively. Hence, at equivalent mole ratios, less cupric oxide is required.

One of the important factors affecting the progress of the Ullmann ether synthesis is the selection of the appropriate ligand system. A recent study, published in Chang, J. W. W. et al Tet. Lett. 2008, 49, 2018-2022, on the reaction to make diaryl ethers without added ligand using phenol and iodobenzene showed that 10% CuI catalyst was needed to achieve yields above 95% and the reaction required 22 hr. Using bromobenzene or less catalyst significantly reduced the yield. In another study, published in Williams, A. L.; Kinney, R. E. and Bridger, R. F. *J. Org. Chem.* 1967, 32, 2501-2505, using resorcinol as the reactant with bromobenzene, Williams showed that the complexing ability of the ligands and the solvent has a significant effect on the course of the reaction. The reaction in pyridine gave 70% yield, whereas the reaction in 91% pyridine/9% 2,2'-bipyridine gave only 31% yield. They interestingly mentioned that excess base in the reaction destroys the catalyst and that they ran the reactions using 95% of stoichiometric base.

There are some other reports on the effects of ligands on the Ullmann ether reaction. Goodbrand, in Goodbrand, H. B. and Hu, N.-X. J. Org. Chem. 1999, 64, 670-674, showed that in the Ullmann reaction for amine synthesis 1,10-phenanthroline added at 3.5% with 3.5% cuprous chloride gave a significant rate acceleration to the reaction. A variety of other ligand studies can be found in the literature, including, for example, Rao, H. et al *Chem. Eur. J.* 2006, 12, 3636-3646; Wang, B.-A. et al *Chinese J. Chem.* 2006, 24, 1062-1065; Ma, D. and Cai, Q. *Org. Lett.* 2003, 5, 3799; Cristau, H.-J. et al *Org. Lett.* 2004, 6(6), 913-916; Ghosh, R. and Samuelson, A. G. *New J. Chem.* 2004, 28, 1390-1393. Some of the ligands mentioned include a variety of pyridine-based structures, dimethylglycine (an amino acid), 2,2,6,6-tetramethylheptane-3,5-dione, imidazoles, etc. One of the ligands, dimethylglycine (DMG) has not been used in the synthesis of polymers or oligomers.

SUMMARY

One aspect of inventive subject matter described herein involves an aryl composition. The aryl composition may comprise aryl ether oligomers. The aryl composition may have the formula:

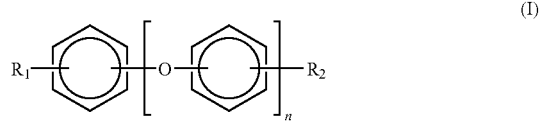

where n is 0 or at least 1; where $R_1$ is OH or halogen; and where $R_2$ is OH, halogen or a phenoxy group of the formula:

where $R_3$ is OH or halogen.

The aryl composition may comprise, for example, 20 wt % or less of compounds of formula (I) with a single benzene ring. Such compounds with a single benzene ring correspond to those of formula (I), where n is 0 and $R_2$ is OH or halogen. The aryl composition may comprise, for example, 30 wt % or less of compounds of formula (I) with two or less benzene rings. Compounds with two benzene rings correspond to those of formula (I), where either (i) n is 1 and $R_2$ is OH or halogen or (ii) both n and $R_2$ are selected such that n is 0 and $R_2$ is a phenoxy group of formula (II). The aryl composition may comprise, for example, 70 wt % or greater of compounds of formula (I) with at least three benzene rings. Compounds with three benzene rings correspond to those of formula (I), where either (i) n is 2 and $R_2$ is OH or halogen or (ii) both n and $R_2$ are selected such that n is 1 and $R_2$ is a phenoxy group of formula (II). The aryl composition comprises a mixture of compounds of formula (I) with three benzene rings and compounds of formula (I) with more than three benzene rings, and the weight of compounds of formula (I) with three benzene rings may be less than the weight of compounds of formula (I) with more than three benzene rings. The average molecular weight of compounds of formula (I) may be at least 400. The compounds of formula (I) may have, on average, at least 2 wt % halogen, for example, from 2 wt % to 35 wt % halogen.

Oligomers where $R_1$, $R_2$ or $R_3$ are OH or halogen may be said to be terminated or endcapped with OH or halogen. When the oligomers have three or more benzene rings, most of the oligomers will be terminated with halogens, rather than with OH. In particular, most of the oligomers with three or more benzene rings will be terminated with two halogens, a lesser number of these oligomers will be terminated with two OH groups, and a few, if any, of these oligomers will be terminated with one halogen and one OH group. Also, of the oligomers having three or more benzene rings, most of these oligomers will have an odd number (e.g., 3, 5, 7, etc.), rather than an even number (e.g., 4, 6, 8, etc.), of benzene rings. The aryl compositions include those prepared by removing compounds with one or two benzene rings. For example, the aryl composition may comprise less than 1.0 wt % of compounds of formula (I) with one benzene ring.

Another aspect of inventive subject matter described herein involves methods for making aryl ether oligomers. The method may comprise reacting one or more dihalobenzenes, such as dibromobenzene, with a salt of one or more dihydroxybenzenes, such as resorcinol. The number of moles of dihalobenzene may exceed the number of moles of the salt of dihydroxybenzene. For example, the ratio of the number of moles of dihalobenzene to the number of moles of the salt of resorcinol may be from about 1.1 to about 1.9, e.g., from about 1.1 to about 1.6.

The catalyst for reacting dihalobenzene with a salt of resorcinol may be a copper containing composition, such as cupric oxide or a cupric salt, such as cupric acetate.

A particular method for preparing aryl ether oligomers involves reacting dihalobenzene with a potassium salt of resorcinol in the presence of a cupric oxide catalyst. The potassium salt of resorcinol may be prepared by the steps of:

(a) preparing a reaction mixture by combining dihalobenzene, resorcinol, KOH (e.g., as solid KOH or an aqueous solution of KOH) and a solvent; and (b) heating the reaction mixture of step (a) to reflux to remove water.

After oligomers are formed, compounds with one benzene ring (e.g., unreacted dihalobenzene or recorcinol) and compounds with only two benzene rings may be removed from the product mixture, for example by washing or distillation or both washing and distillation, to obtain an oligomeric product, wherein the oligomers have three or more benzene rings. Examples of steps used to recover an oligomer product, formed by reacting dibromobenzene with a potassium salt of rescorcinol, include the steps of:

(c) removing KBr salts from the product mixture of step (b) by filtration;

(d) stripping the solvent from the product mixture of step (c) to form an organic residue;

(e) washing the organic residue of step (d) with a dilute aqueous solution of a base (e.g., NaOH) followed by water washing; and (f) removing residual dibromobenzene from the washed organinc residue of step (e) by distillation.

DESCRIPTION OF THE EMBODIMENTS

The aryl compositions described herein, especially the aryl oligomers described herein, may be used as intermediates to form flame retardant compositions. In particular, these aryl compositions may be brominated to form flame retardant compositions, especially for flammable macromolecular polymers. Such macromolecular polymers include thermoplastic polymers, such as polystyrene, poly (acrylonitrile butadiene styrene), polycarbonates, polyolefins, polyesters and polyamides, and thermosetting polymers, such as epoxy resins, unsaturated polyesters, polyurethanes and rubbers. Methods for brominating aryl compositions to make flame retardant compositions, as well as methods for using such brominated aryl compositions as flame retardants for thermoplastic polymers, are described in United States Patent Application Publication Number US 2008/0269416, which corresponds to International Publication Number WO 2008/134294, the bromination method descriptions thereof being expressly incorporated herein by reference.

The term "oligomer" is used herein to mean a compound formed by oligomerization of one or more monomers so as to have repeating units derived from said monomer(s) irrespective of the number of said repeating units. The oligomers will have a distribution of molecular weight. In particular, an oligomer formed by method described herein may have an average of least 3 benzene rings. The average molecular weight of these oligomers, especially those where halogen is Br, may be at least 400 grams per mole, for example, at least 600 grams per mole, for example, at least 800 grams per mole. Molecular weight may be measured by GPC chromatography vs polystyrene standards.

The compounds of formula (I), particularly, the compounds of formula (I) having two or more benzene rings, especially, the compounds of formula (I) having three or more benzene rings, may have, on average, from 2 wt % to 35 wt % halogen. In other words, the weight of chemically bound halogen in the compounds of formula (I), based upon the entire weight of the compounds of formula (I), may be from 2 wt % to 35 wt %, for example, from 5 wt % to 30 wt %, for example, from 10 wt % to 25 wt %.

The aryl compositions described herein may comprise a mixture of (1) unreacted monomers used to prepare oligomers and (2) oligomers produced from these monomers. These unreacted monomers may include dihalobenzene, particularly at least one dibromobenzene, such as 1,2-dibromobenzene (i.e. ortho-dibromobenzene), 1,3-dibromobenzene (i.e. meta-dibromobenzene), or 1,4-dibromobenzene (i.e. para-dibromobenzene) or mixtures thereof. The unreacted monomers may also include a dihydroxybenzene, such as 1,2-dihydroxybenzene (i.e. pyrocatechol or ortho-dihydroxybenzene), 1,3-dihydroxybenzene (i.e. resorcinol, recorcin, meta-dihydroxybenzene or 3-hydroxyphenol)), or 1,4-dihydroxybenzene (i.e. hydroquinone or para-dihydroxybenzene) or mixtures thereof.

An aryl composition formed by reacting dibromobenzene with a dihydroxybenzene may have the formula:

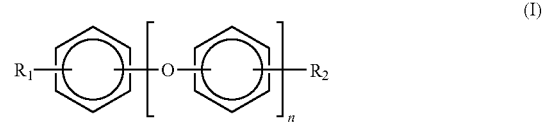

(I)

where n is 0 or at least 1; where $R_1$ is OH or Br; and where $R_2$ is OH, Br or a phenoxy group of the formula:

(II)

where $R_3$ is OH or Br. To facilitate this reaction, the dihydroxybenzene is usually converted from a free base into the form of a salt. However, after the reaction, the free base form may be regenerated.

The reaction product formed by reacting dihalobenzene with a dihydroxybenzene may have a limited amount of light ends, that is, a relatively small amount of unreacted monomers and dimers (i.e. compounds with two benzene rings). For example, the aryl composition of formula (I) may comprise 30 wt % or less, e.g., 20 wt % or less, e.g., 10 wt % or less, of compounds with one benzene ring and/or two benzene rings. The unreacted monomers may be present in the product mixture at a concentration of, for example, less than 1% by weight, of the entire aryl composition. Optionally, the unreacted monomers (e.g., dibromobenzene or dihydroxybenzene, which are compounds with only a single benzene ring)

may be removed from the reaction product altogether or at least to a concentration of less than 0.1% by weight of the entire aryl composition, by a separation technique, such as distillation. Species of monomers and oligomers, especially dimers, which contain hydroxyl groups can also be removed by washing a reaction product with an aqueous base, such as NaOH, followed by washing the product with water. Especially after such washing treatment, the resulting aryl composition of formula (I) may comprise less than 2% by weight of compounds with two or less benzene rings. Recovered unreacted monomers and recovered dimers may be recycled and fed into the oligomerization reactor along with fresh reactant feed.

The reaction product formed by reacting dihalobenzene, such as dibromobenzene, with a dihydroxybenzene may have a relatively large amount of medium and heavy ends, that is, compounds having 3 or more benzene rings. Such medium and heavy ends may comprise 80 wt % or greater of compounds of formula (I). However, the heavy ends of this mixture may be restricted. For example, the reaction product formed by reacting dibromobenzene with a dihydroxybenzene may have less than 80 wt % of compounds of formula (I) with five or more benzene rings.

The reaction product formed by reacting dibromobenzene with a dihydroxybenzene may have, for example, a molecular weight of Mw=600-2000 and a polydispersity of 1.4-2.5 as measured by GPC chromatography vs polystyrene standards.

The compounds of formula (I) may have terminal halogen substituents and terminal hydroxyl substituents. There may be more terminal halogen substituents, i.e. compounds where $R_1$, $R_2$ or $R_3$ in formula (I) are halogen, than terminal hydroxyl substituents, i.e. compounds where $R_1$, $R_2$ or $R_3$ in formula (I) are OH. Such compounds with an excess of halogen groups relative to OH groups may be made by reacting a molar excess of dihalobenzene with a molar deficiency of dihydroxybenzene (e.g., resorcinol). For example, such compounds may be formed when the molar ratio of dihalobenzene to dihydroxybenzene (e.g., resorcinol) in an appropriate reaction mixture for combining such compounds is from about 1.1:1 to about 1.9:1, e.g., from about 1.1:1 to about 1.6:1.

It is possible that a small quantity of unintended products, for example, 1 percent by weight or less, may result from side reactions. Such side reactions may result in small amounts of oligomers lacking a terminal OH or halo group (e.g., compounds of formula (I) where $R_2$ or $R_3$ is hydrogen), or where internal phenylene groups are directly connected to form a biphenyl linkage. It is also possible that a small amount of cyclic oligomeric products are produced in addition to the main linear molecules described by formula (I).

Particularly when recorcinol (i.e. 1,3-dihydroxybenzene) is used as a reactant, the compounds of formula (I) may have meta phenylene groups in the oligomers.

In order to facilitate the reaction of dihalobenzene with dihydroxybenzene, a catalyst and a base are typically used. The base is capable of displacing protons from acidic phenol groups (i.e. hydroxyl groups) on dihydroxybenzenes. The displaced protons may be substituted with cations, particularly monovalent cations, from the base to form a salt. An example of a particular base is potassium hydroxide. The dihydroxybenzene may be converted into a salt prior to introducing the catalyst into the reaction mixture. The salts of dihydroxybenzene may be mono-salts (i.e. compounds having one terminal monovalent cation and one terminal hydroxyl group) or di-salts (i.e. compounds having two terminal monovalent cations and no terminal hydroxyl groups) or mixtures of mono-salts and di-salts.

The dihalobenzene and dihydroxybenzene used to form oligomers may be individual isomers of these compounds or mixtures thereof. An example of a mixture of dibromobenzene isomers is a mixture of 1,2-, 1,3- and 1,4-dibromobenzene in a weight or molar ratio of 10:45:45.

The total number of moles of dihalobeneze used in the reaction may exceed the total number of moles of dihydroxybenzene. The use of such a molar excess of dihalobenzene promotes the formation of oligomers with more terminal halogen groups than terminal hydroxyl groups. The molar ratio of dihalobenzene (including mixtures of dihalobenzene isomers) to the molar ratio of dihydroxybenzene (including mixtures of dihydroxybenzene isomers) may be from about 1.1: to about 1.9:1, for example, from about 1.1:1 to about 1.6:1. In calculating these ratios, it will be understood that the dihydroxybenzenes may be in a protonated form, e.g., prior to contact with a base, or in a salt form, which is formed after contact with a base. Compositions which can be used as a base to form a salt of a dihydroxybenzene include KOH, NaOH, $K_2CO_3$, $Cs_2CO_3$ and $K_3PO_4$. These base compositions may be added to the reaction mixture in the form of a solution, such as an aqueous solution, or in the form of a solid.

A salt of dihydroxybenzene may be prepared by forming a mixture of dihydroxybenzene, an aqueous solution of a base and a solvent. This mixture may also include dihalobenzene and/or a liquid capable of forming an azeotrope with water. This mixture may then be heated to reflux to azeotropically remove water. The liquid capable of forming an azeotrope with water may be toluene. The solvent may be dimethylformamide. The number of monovalent cations in the base to the number of protons in hydroxyl groups of the dihydroxybenzene may be from about 0.9:1 to about 1.25:1. For example, when KOH is used as the base, the molar ratio of KOH to dihydroxybenzene may be from about 1.8:1 to about 2.5:1, for example, from about 2.1:1 to about 2.5:1. At least 50% of the liquid capable of forming an azeotrope may be stripped from the reaction mixture along with the water which is azeotropically removed. Optionally, the liquid capable of forming an azeotrope with water may be omitted, and water may be distilled out of the reaction directly. The dihalobenzene and dihydroxybenzene reactants may be added to the reaction mixture all at once or in stages. As an example of a staged addition, a first portion of the dihalobenzene reactant may be added to the reaction mixture initially, oligomers may be formed, and then the final portion of the dihalobenzene may be added to the reaction mixture.

The catalyst used in the reaction to form compounds of formula (I) may be a copper containing catalyst. Examples of such copper containing catalysts include copper (I) compounds (i.e. cuprous compounds) and copper (II) compounds (i.e. cupric compounds). These compounds may be oxides or salts. Particular examples of copper containing catalysts include CuI, CuBr, $Cu_2O$, CuO and cupric acetate. The molar ratio of copper containing catalyst to the dihydroxybenzene (whether in the protonated form or in the form of a salt) may be, for example, from about 0.01:1 to about 0.04:1.

The copper containing catalyst may be incorporated into the reaction mixture at any convenient stage. For example, the copper containing catalyst may be added to the reaction mixture after water has been removed, for example, by azeotropic stripping as described above. Optionally, the copper containing catalyst may be added to the reaction mixture before water removal.

The reaction mixture including dibromobenzene, dihydroxybenzene (optionally in the form of a salt) and catalyst may be reacted under conditions to form oligomers of formula (I). These conditions may include a temperature above 140° C., preferably above 150° C., with a reaction time of at least five hours.

The copper containing catalyst may optionally be combined with a ligand to promote the formation of oligomers of formula (I). Examples of such ligands include 1,10-phenanthroline, dimethylglycine, 1-butylimidazole, 1-methylimidazole and DL-alanine. The molar ratio of copper containing catalyst to ligand may be from 1:3 to about 3:1.

The product of the reaction may be recovered by any convenient means. For example, when a potassium salt of a dihydroxybenzene is used as a reactant a byproduct of the reaction is KBr. This KBr salt may be removed from the product mixture by filtration. The solvent may then be stripped from the reaction mixture to form an organic residue. The residue may be dissolved in a water-immiscible solvent if needed. This organic residue may then be washed with dilute aqueous base, such as NaOH, followed by water washing to remove any free phenolic-terminated oligomeric chains. This wash stream may be recycled back into a subsequent reaction to improve the yield. Optionally, the reaction mixture may be terminated by addition of an aryl halide such as bromobenzene toward the end of the reaction hold period to help to minimize the amount of free phenolic-terminated oligomer chains. Finally, residual dibromobenzene and/or bromobenzene and resorcinol low-boiling materials may be removed from the washed organic residue by distillation. Reactive materials recovered by distillation may be recycled back into a reaction mixture as appropriate.

EXAMPLES 1 to 15

Copper Catalyst Screening

In Examples 1-15, various copper catalyst systems were screened for the polymerization of resorcinol (RC) and para-dibromobenzene (PDBB) as indicated in Table 1. It will be understood that para-dibromobenzene (PDBB) is the same compound as 1,4-dibromobenzene. The reactions were conducted under the following conditions:

Equimolar amounts of RC and PDBB were charged to a reaction flask under nitrogen. Dimethylformamide (DMF) (12.6 g/g RC) and toluene (3 g/g RC) were added followed by an aqueous solution of KOH (2.0 mol/mol RC). After the initial exotherm, the reaction was heated to reflux to azeotropically remove the water. Then, the toluene was removed by continued distillation until the reflux temperature of DMF was reached (153° C.). Anhydrous DMF was added back to the reaction flask to supplant any DMF that was distilled during the toluene strip to maintain the 12.6 g DMF/g RC ratio. Then, the catalyst was added and the reaction was held at reflux for 20 hr before sampling for analysis.

The samples were analyzed by high pressure liquid chromatography (HPLC). The HPLC analysis shows a series of peaks that correspond to various oligomeric chains based on the number of aryl (i.e. benzene) rings. There were several peaks present at each chain length and further examination revealed the different nature of the end groups on the oligomer chains. The nature of the HPLC peaks was confirmed by mass spectrometry. It was found that the different species present for the major components were chain-terminated by aryl bromide or by aryl hydroxide, or to a lesser degree by aryl-hydrogen. These could be seen up through ~8 ring species, with the higher molecular weight oligomers co-eluting at the end of the chromatogram.

For purposes of making an oligomeric flame retardant material, it would be desirable to maximize the amount of 3-ring species and larger and to minimize the amount of 2-ring species (dimer) and starting material compounds. These groups of materials were tracked as a whole in the HPLC analysis in Table 1 by HPLC area %.

TABLE 1

Aryl Ether Oligomer Preparations Using Different Copper Catalysts.

| Example No. | Catalyst Type | Mol %[b] | HPLC wt % RC | HPLC wt % PDBB | HPLC A %[a] ≦2-Ring | HPLC A %[a] ≧3-Ring |
|---|---|---|---|---|---|---|
| 1 | CuI | 2 | 0.13 | 0.0 | 24.0 | 76.0 |
| 2 | CuI | 2 | 0.20 | 0.0 | 23.8 | 76.2 |
| 3 | CuI | 4 | 0.0 | 0.0 | 9.6 | 90.4 |
| 4 | CuCl | 2 | 0.11 | 0.3 | 38.3 | 61.7 |
| 5 | CuCl | 2 | 0.98 | 0.7 | 49.7 | 50.3 |
| 6 | CuBr | 2 | 0.92 | 7.2 | 91.1 | 8.9 |
| 7 | CuBr | 2 | 2.40 | 7.2 | 93.0 | 7.0 |
| 8 | CuCl$_2$ | 2 | 0.32 | 0.5 | 45.4 | 54.6 |
| 9 | Cu$_2$O | 2 | 0.0 | 0.0 | 18.0 | 82.0 |
| 10 | Cu$_2$O | 4 | 0.02 | 0.0 | 9.8 | 90.2 |
| 11 | CuO | 2 | 0.0 | 0.0 | 17.7 | 82.3 |
| 12 | CuO | 4 | 0.0 | 0.0 | 13.0 | 87.0 |
| 13 | CuO | 6 | 0.0 | 0.0 | 15.7 | 84.3 |
| 14 | CuO | 8 | 0.0 | 0.0 | 13.2 | 86.9 |
| 15 | CuO | 10 | 0.0 | 0.0 | 14.5 | 85.5 |

[a]Reactions were sampled for HPLC area % analysis after 20 hr at reflux. Samples were worked up by shaking with dilute HCl and methylene chloride. Weight % analysis was conducted using an external standard.
[b]Mol % based on moles RC used.

The data in Table 1 show that CuCl, CuCl$_2$ and, especially, CuBr, produce the least amount of desired product peaks (≧3-ring species). At 2 mol % usage, the CuO and Cu$_2$O performed slightly better than the CuI, giving ~82% product. At 4 mol %, those catalysts systems gave 87.0, 90.2, and 90.4% product, respectively. Using more than 4 mol% CuO gave no added benefit.

EXAMPLES 16 to 48

Catalyst and Ligand Screening Reactions

The aryl ether coupling reaction was further conducted using the copper catalysts with additional ligand materials, as shown in Table 2. The reaction conditions were identical to that described in Examples 1-15.

TABLE 2

Aryl Ether Oligomer Preparations Using Copper Catalysts With Various Ligands.

| Example No. | Catalyst | Ligand | Cat/L, Mol %[b] | HPLC A % Analysis[a] ≦2-Ring | HPLC A % Analysis[a] ≧3-Ring |
|---|---|---|---|---|---|
| 16 | CuI | None | 4/0 | 9.6 | 90.4 |
| 17 | " | 1,10-phenanthroline | 2/3 | 10.0 | 90.0 |
| 18 | " | 1,10-phenanthroline | 3/2 | 10.4 | 89.6 |
| 19 | " | Triphenylphosphine | 2/2 | 21.9 | 78.1 |
| 20 | " | Triphenylphosphine | 2/3 | 28.2 | 71.8 |
| 21 | " | ethyleneglycol diacetate | 2/3 | 19.8 | 80.2 |
| 22 | " | Ethylenediamine | 2/3 | 34.2 | 65.8 |
| 23 | " | Ethylenediamine | 3/2 | 36.6 | 63.4 |
| 24 | " | Pyridine | 2/2 | 20.6 | 79.5 |
| 25 | " | Pyridine | 2/3 | 24.2 | 75.8 |
| 26 | " | 1,2-dimethoxyethane | 2/2 | 20.8 | 79.2 |
| 27 | " | 1,2-dimethoxyethane | 2/3 | 19.5 | 80.5 |
| 28 | " | Diglyme | 2/2 | 19.7 | 80.3 |
| 29 | " | Diglyme | 2/3 | 23.6 | 76.4 |
| 30 | " | 1-butylimidazole | 2/4 | 21.8 | 78.2 |
| 31 | Cu$_2$O | None | 4/0 | 9.8 | 90.2 |
| 32 | " | 1,10-phenanthroline | 2/1.3 | 11.3 | 88.7 |
| 33 | " | 1,10-phenanthroline | 2/3 | 9.3 | 90.7 |
| 34 | " | 1,10-phenanthroline | 3/2 | 9.0 | 91.0 |
| 35 | " | 1,10-phenanthroline | 4/2.7 | 10.8 | 89.2 |
| 36 | " | 1,10-phenanthroline | 4/6 | 8.5 | 91.5 |

TABLE 2-continued

Aryl Ether Oligomer Preparations Using Copper Catalysts With Various Ligands.

| Example No. | Cata- lyst | Ligand | Cat/L, Mol %[b] | HPLC A % Analysis[a] ≦2-Ring | ≧3-Ring |
|---|---|---|---|---|---|
| 37 | " | Dimethylglycine | 2/3 | 13.1 | 86.9 |
| 38 | " | Triphenylphosphine | 2/3 | 19.2 | 80.8 |
| 39 | " | Ethylenediamine | 3/2 | 18.5 | 81.5 |
| 40 | CuO | None | 4/0 | 13.0 | 87.0 |
| 41 | " | 1,10-phenanthroline | 2/1.3 | 13.4 | 86.6 |
| 42 | " | 1,10-phenanthroline | 2/3 | 9.1 | 90.9 |
| 43 | " | 1,10-phenanthroline | 3/2 | 10.6 | 89.4 |
| 44 | " | 1,10-phenanthroline | 4/2.7 | 9.8 | 90.2 |
| 45 | " | 1,10-phenanthroline | 4/6 | 8.8 | 91.2 |
| 46[c] | " | Dimethylglycine | 3/2 | 2.6 | 97.4 |
| 47 | " | Ethylenediamine | 3/2 | 18.4 | 81.6 |
| 48 | " | 1-butylimidazole | 2/4 | 30.4 | 69.6 |

[a]Reactions were sampled for HPLC area % analysis after 20 hr at reflux. Samples were worked up by shaking with dilute HCl and methylene chloride.
[b]Mol % based on moles RC used.
[c]Used 1.55 mol PDBB, 24-hr sample.

The Table 2 data indicate that 1,10-phenanthroline (phen) and dimethylglycine (DMG) showed the most potential for use as ligands to give a product with the maximum amount of oligomeric components that were ≧3-ring species. Using catalyst at 4 mol % without ligand gave about the same amount of product as the system using 2 mol % catalyst plus ligands. Thus, the use of certain ligands allows the amount of copper catalyst to be reduced. The use of CuO (a copper (II) species) gave results that were at least as good as when the copper (I) catalysts were used at equivalent mol % use levels. This provides a significant advantage in molecular weight vs. the Cu(I) catalysts and therefore provides a lower overall use level and economic advantage.

EXAMPLES 49 to 68

Catalyst and Ligand Screening Reactions with Aryl Endcapping

The optimization reactions conducted for Table 1 and Table 2 employed a RC:PDBB stoichiometry of 1:1. This 1:1 ratio would theoretically generate the highest molecular weight possible with this type of system. However, that type of reaction would leave a large amount of oligomer chains with OH-terminated sites. These OH-terminated sites may be useful for subsequent chemical reactions, but these OH-terminated sites may be detrimental to the use of these oligomers, especially brominated products thereof, as flame retardant compounds.

In an effort to reduce the amount of OH-terminated sites, the reaction stoichiometry was altered to allow excess PDBB in the reaction. In this case, the PDBB could function as both a chain extender and as an endcap. Tracking of the endcapping efficiency was conducted by HPLC analysis and examination of the different 3-ring species that are formed, which include bromo endcapped or hydroxy endcapped compounds. The trends in endcapping efficiency for these 3-ring components would be similar to those seen for the system as a whole.

The reaction conditions for Table 3 are as follows: RC and PDBB were charged to a reaction flask under nitrogen at the indicated mol ratios. DMF (12.6 g/g RC) and toluene (3 g/g RC) were added followed by an aqueous solution of KOH (2.0 mol/mol RC). After the initial exotherm, the reaction was heated to reflux to azeotropically remove the water. Then, the toluene was removed by continued distillation until the reflux temperature of DMF was reached (153° C.). Anhydrous DMF was added back to the reaction flask to supplant any DMF that was distilled during the toluene strip to maintain the 12.6 g DMF/g RC ratio. Then, the catalyst was added and the reaction was held at reflux for 20 hr before sampling for analysis.

TABLE 3

Effect of RC:PDBB Stoichiometry and Catalyst/Ligand System on Oligomer Formation and Endcapping.

| Example No. | RC:DBB mol ratio | Cat. | Ligand[b] | Cat/L Mol %[c] | HPLC A % Analysis[a] ≦2-Ring | ≧3-Ring | 3-Ring Only | % Endcap Type in 3-Ring Components Br | OH |
|---|---|---|---|---|---|---|---|---|---|
| 49 | 1:1.0 | CuO | none | 4/0 | 13.0 | 87.0 | 20.0 | 49.5 | 50.5 |
| 50 | 1:1.5 | CuO | none | 4/0 | 14.2 | 85.8 | 17.3 | 87.9 | 12.1 |
| 51 | 1:1.0 | CuO | phen | 2/3 | 9.1 | 90.9 | 23.1 | 52.4 | 47.6 |
| 52 | 1:1.5 | CuO | phen | 2/3 | 15.7 | 84.3 | 25.0 | 95.2 | 4.8 |
| 53[d] | 1:1.5 | CuO | DMG | 2/3 | 8.7 | 91.3 | 28.2 | 98.6 | 1.4 |
| 54 | 1:1.5 | CuO | DMG | 2/3 | 4.8 | 95.2 | 25.3 | 99.2 | 0.8 |

[a]Reactions were sampled for HPLC area % analysis after 20 hr at reflux. Samples were worked up by shaking with dilute HCl and methylene chloride.
[b]phen = 1,10-phenanthroline; DMG = dimethylglycine
[c]Mol % based on moles RC used.
[d]Reaction time was 10 hr.

The data in Table 3 show that the use of an excess of PDBB increases the amount of bromine-terminated 3-ring oligomer groups and significantly decreases the amount of hydroxyl-terminated chains. The data also shows that the amount of hydroxyl-terminated chains is reduced even further when the DMG ligand system was used and that the reaction time could be decreased to less than 10 hr. Some additional catalyst and ligand systems were evaluated at the 1:1.5 RC:PDBB mol ratio, as shown in Table 4, under the same reaction conditions as in Table 3.

The CuO catalyst system data in Tables 3 and 4 indicates that dimethylglycine (DMG) gives the most amount of ≧3-ring oligomers in the shortest reaction time. Several of the other ligands also performed well, such as the imidazoles, the dimethylglyoxime, the sarcosine and the DL-alanine.

In Examples 64-66, cupric acetate was used as a "soluble" (homogeneous) copper catalyst system both with and without added ligands and showed very good performance in this reaction. The performance was enhanced further with DMG ligand in combination. In Examples 67 and 68, two heterogeneous copper catalysts (Cu/alumina and Cu/Pd on C) gave only 12% and 1% of components containing 3-rings or greater at 20-hr reaction time.

to supplant some DMF that was distilled during the toluene strip to achieve 9.0 g DMF/g RC ratio. For the other bases, the toluene was used and distilled, but no water was observed in the azeotrope, as expected. The amount of base was 2.25 mol/mol RC in all cases. Then, the CuO (0.02 Eq) and DMG (0.03 Eq) were added and the reactions were held at reflux for 8 hr. A sample was removed and isolated by methylene chloride/5% HCl washing and the organic layer was analyzed by HPLC.

TABLE 4

Additional Catalyst/Ligand Screening at the 1:1.5 RC:PDBB Mol Ratio.

| Example No. | Cat. | Ligand[c] | Cat/L Mol %[b] | Rx'n time, hr | HPLC A % Analysis[a] ≦2-Ring | ≧3-Ring | 3-Ring Only | % Endcap Type in 3-Ring Components Br | OH |
|---|---|---|---|---|---|---|---|---|---|
| 55 | CuO | 1-Butylimidazole | 2/3 | 20 | 14.5 | 85.5 | 23.6 | 90.7 | 9.3 |
| 56 | " | 1-Methylimidazole | 2/3 | 20 | 16.0 | 84.0 | 27.2 | 93.0 | 7.0 |
| 57 | " | Dimethylglyoxime | 2/3 | 20 | 13.2 | 86.8 | 23.7 | 89.5 | 10.5 |
| 58 | " | Glycine | 2/3 | 8 | 84.4 | 14.6 | 13.1 | 93.1 | 6.9 |
| 59 | " | Sarcosine | 2/3 | 8 | 27.9 | 72.1 | 37.3 | 95.7 | 4.3 |
| 60 | " | DL-Alanine | 2/3 | 8 | 16.3 | 83.7 | 33.3 | 95.8 | 4.2 |
| 61 | " | EDTA | 2/3 | 8 | 93.1 | 6.9 | 5.9 | 10.2 | 89.8 |
| 62 | " | Proline | 2/3 | 2/3 | 41.7 | 58.3 | 36.4 | 95.9 | 4.1 |
| 63 | " | Nitrilotriacetic acid | 2/3 | 8 | 58.8 | 41.3 | 29.3 | 5.5 | 94.5 |
| 64 | $Cu(CO_2CH_3)_2$ | none | 4/0 | 20 | 9.7 | 90.3 | 16.7 | 94.0 | 6.0 |
| 65 | " | Dimethylglycine | 2/3 | 8 | 2.7 | 97.3 | 28.2 | 99.3 | 0.7 |
| 66 | " | phen | 2/3 | 20 | 8.3 | 91.7 | 23 | 92.6 | 7.4 |
| 67 | Cu/alumina | none | 13/0 | 20 | 88.0 | 12.0 | 11.1 | 91.9 | 8.1 |
| 68 | Cu/Pd on C | none | 4/0 | 20 | 99.0 | 1.0 | 0.1 | 0.0 | 100.0 |

[a]Reactions were sampled for HPLC area % analysis after 20 hr at reflux unless otherwise indicated. Samples were worked up by shaking with dilute HCl and methylene chloride.
[b]Mol % based on moles RC used.
[c]phen = 1,10-phenanthroline EXAMPLES 69 to 80

Type of Base and Effect on Yield

There are many references in the literature that indicate the use of anhydrous carbonate bases or phosphate can be used in Ullmann ether coupling reactions. In fact, many Ullmann ether coupling reactions disclose the need for using $Cs_2CO_3$ as the base for giving improved reaction rates and yields. In Examples 69-80, the effects of the various bases on the reaction were compared by analyzing the reaction mixtures after 8 hr reflux in DMF solvent, as shown in Table 5.

For these reactions, RC (1.0 Eq) and PDBB (1.55 Eq) were charged to a reaction flask under nitrogen. DMF (12.6 g/g RC) was used as the solvent. For the hydroxide bases, toluene (3 g/g RC) was added followed by an aqueous solution of the base (2.25 mol/mol RC). After the initial exotherm, the reaction was heated to reflux to azeotropically remove the water. Then, the toluene was removed by continued distillation until the reflux temperature of DMF was reached (153° C.). Anhydrous DMF was added back to the reaction flask if necessary

TABLE 5

Effect of Various Bases on Oligomer Reaction.

| Example No. | Base | HPLC A % Analysis ≦2-Ring | ≧3-Ring |
|---|---|---|---|
| 69 | KOH | 3.1 | 96.9 |
| 70 | NaOH | 94.4 | 5.6 |
| 71 | $K_2CO_3$ | 9.9 | 90.1 |
| 72 | $Cs_2CO_3$ | 58.5 | 41.5 |
| 73 | $K_3PO_4$ | 45.8 | 54.2 |

In Example 69, which used KOH as the base, the highest amount of oligomers with at least three benzene rings was formed vs. the other bases tested. In contrast, the sodium hydroxide reaction (Example 70) produced the least amount of oligomers with at least three benzene rings and produced a very high level of 2-ring species.

Next, KOH stoichiometry was varied to determine the effect on yield, as shown in Table 6. The reactions were conducted as described in Examples 69-73. The material was worked up by filtering the KBr salts, stripping the DMF and washing the organic residue in a solvent with dilute NaOH followed by water washing and then distillation of any residual starting material. This method gives an oligomer essentially free of OH-terminated species.

TABLE 6

Effect of KOH Stoichiometry on Yield for 8-hr Reaction.

| | | | Crude Product[a] | | Final Product[b] | |
|---|---|---|---|---|---|---|
| | | | HPLC Area % Analysis | | | |
| Example No. | KOH Eq on RC | % Yield[c] | % OH Terminated Oligomers[d] | ≧3-Ring | % OH Terminated Oligomers[c] | ≧3-Ring |
| 74 | 2.00 | 66.0 | 14.5 | 90.4 | 2.2 | 99.4 |
| 75 | 2.05 | 72.3 | 7.7 | 94.8 | 2.0 | 99.6 |
| 76 | 2.15 | 83.0 | 6.6 | 95.0 | 2.3 | 99.2 |
| 77 | 2.25 | 90.0 | 2.4 | 96.5 | 1.5 | 99.6 |
| 78 | 2.25 | 92.0 | 1.9 | 97.8 | 1.1 | 99.3 |
| 79 | 2.30 | 89.0 | 3.8 | 96.6 | 1.6 | 99.7 |
| 80[e] | 2.25 | 68.0 | 13.2 | 91.2 | 1.4 | 99.5 |

[a]Before base washing.
[b]After base washing
[c]In-hand mass yield after base washing. For Yield calculation, see end of Experimental section.
[d]Area % sum of all identifiable HPLC species containing at least one OH terminal group at 3-rings or greater.
[e]Reaction stopped after 6 hr.

The yield vs. KOH equivalents data clearly show an improvement in yield up to approximately 2.25 equivalents of KOH. The higher amount of KOH apparently allows more complete utilization of the PDBB as endcap, thus minimizing the amount of OH-terminated materials that would be removed by base-washing, resulting in a higher overall yield.

EXAMPLES 81 to 90

Optimization of Reaction Concentration and Solvent Choice

In Examples 81-88, a variety of solvents was used in reactions involving 1:1 RC:PDBB stoichiometry. Results are shown in Table 7. If the solvent would allow a water-removal step by azeotrope, KOH was used as the base. If the solvent was not amenable to that technique, a phosphate or carbonate base was used.

A factor in having some solvents work better than others is related to the solubility of the resorcinol salt in the solvent medium. Those solvents that did not dissolve the resorcinol salt very well generally gave poor results. Some of the solvents gave good results in terms of product assay by HPLC, but when the carbonate or phosphate base was used, the reaction system became a thick slurry, rendering the product isolation very problematic.

In Examples 89 and 90, solvent concentration was varied using DMF as the solvent. Results are shown in Table 8. These reactions were run at the 1:1.55 RC:PDBB stoichiometry. The data shows that the reaction proceeds to a high conversion to ≧3-ring products in both cases, but the amount of OH-terminated material is lower at the higher concentration, i.e. the reaction progressed further in the same time frame for the more concentrated run.

TABLE 8

Effect of Solvent Concentration on Oligomer Reaction Using DMF.

| | | HPLC A % Analysis[a] | | |
|---|---|---|---|---|
| Example No. | DMF g/g RC | ≦2-ring | ≧3-ring | OH terminated ≧ 3-ring[b] |
| 89 | 12.6 | 2.5 | 97.5 | 7.7 |
| 90 | 9.0 | 3.1 | 96.9 | 1.1 |

[a]Samples were worked up by shaking with dilute HCl and methylene chloride.
[b]Area % sum of all identifiable HPLC species containing at least one OH terminal group at 3-rings or greater.

Comparative Examples to Quantify Oligomeric Molecular Weight Distributions

A representative example (Example 77) at a preferred reaction stoichiometry (PDBB/RC=1.55) described earlier and some new examples were compared and analyzed in detail to determine the influence of the main reaction parameters on the molecular weight distribution, as shown in Table 9. The reactions were run as described earlier for Example 77 unless otherwise indicated. The data shows the molecular weight as measured by GPC vs polystyrene standards. The data also shows the HPLC area % analysis of the individual groupings of the different molecular weight species that were resolved in the chromatogram. The determination of these peaks was done based on separate LCMS analyses.

TABLE 7

Effect of Various Solvent Systems on the Oligomer Reaction.

| Example No. | Solvent Type | Usage g/g RC | Base | Catalyst | HPLC A % Analysis ≦2-Ring | ≧3-Ring |
|---|---|---|---|---|---|---|
| 81 | DMF | 12.6 | KOH | CuI/phen | 9.1 | 90.9 |
| 82 | DMAc[a] | 12.6 | $K_2CO_3$ | CuI/phen | 16 | 84.0 |
| 83 | veratrol | 12.6 | KOH | CuI/phen | 5.5 | 94.5 |
| 84 | 1,3-Dimethoxy benzene | 12.6 | $K_2CO_3$ | CuI/phen | 47.5 | 52.5 |
| 85 | sulfolane | 12.6 | $K_2CO_3$ | CuI/phen | 13.4 | 86.6 |
| 86 | diglyme | 3.0 | $K_3PO_4$ | $Cu_2O$ | 26.3 | 73.7 |
| 87 | butyldiglyme | 4.7 | $K_3PO_4$ | $Cu_2O$ | 97.5 | 2.5 |
| 88 | xylene[b] | 2.7 | $K_3PO_4$ | CuCl | 10.2 | 89.8 |

[a]Dimethylacetamide.
[b]Reactions run with KOH formed a crust on the reactor walls, resulting in no reaction.

TABLE 9

HPLC Analysis of Various Aryl Ether Oligomer Reactions.

| | | Mol Ratios | | | Lights vs Oligomers | | Individual Peak Groupings[a] | | | | | | | |
|---|---|---|---|---|---|---|---|---|---|---|---|---|---|---|
| Ex No | Base washed | KOH/ RC | PDBB/ RC | Mw by GPC | ≦2- ring | ≧3- ring | 3- ring | 4- ring | 5- ring | 6- ring | 7- ring | 8- ring | 9- ring | ≧10- ring |
| 77A | no | 2.25 | 1.55 | n/a | 3.5 | 96.5 | 31.0 | 0.0 | 27.0 | 1.0 | 18.0 | 1.0 | 10.0 | 5.0 |
| 77B | yes | 2.25 | 1.55 | 680 | 0.4 | 99.6 | 30.0 | 0.0 | 25.0 | 1.0 | 17.0 | 0.0 | 10.0 | 5.0 |
| 91[b] | yes | 2.25 | 1.55 | 1280 | 0.7 | 99.3 | 25.9 | 0.0 | 22.5 | 0.0 | 9.7 | 0.3 | 4.8 | 14.5 |
| 92 | yes | 2.00 | 2.00 | 360 | 1.3 | 98.7 | 54.8 | 0.7 | 24.3 | 1.0 | 8.5 | 0.2 | 2.2 | 0.0 |

[a]HPLC area peaks at less than 1% were not included.
[b]One equivalent of PDBB was added at the beginning of the reaction and the remaining PDBB was added at 3 hr reaction time.

In the HPLC analysis from Table 9, the ratios of the various oligomeric chain lengths can be prepared to determine how the material compares to other oligomeric compounds. The ratios based on this analysis should be comparable to actual weight % ratios as a first approximation. The HPLC areas for the Examples of Table 9 show that the amount of oligomers with more than 3 benzene rings exceeded the amount of oligomers with 3 benzene rings when the ratio of para-dibromobenzene to resorcinol was 1.55 to 1. In contrast, HPLC areas for Example 92 of Table 9 show that the amount of oligomers with 3 benzene rings exceeded the amount of oligomers with more than 3 benzene rings when the ratio of para-dibromobenzene to resorcinol was 2.0 to 1.

EXAMPLES 93 to 96

Organic Halogen Content

Reactions were conducted to determine the effects of the RC:PDBB stoichiometry on the organic bromine (oBr) content, since using excess PDBB to function as an endcap would generate a product with a higher amount of organic bromine. The reaction procedure was the same as described for Examples 49-68, and the results are shown in Table 10. Also shown is an estimated organic chlorine (oCl) and organic iodine (oI) level that would be expected if aryl chlorides or aryl iodides were substituted for the aryl bromides that were used. It will be understood that organic bromine, organic chlorine and organic iodine (i.e. oBr, oCl and oI) means Br, Cl and I, which is chemically (i.e. covalently) bound to compounds of formula (I).

These data show that using excess PDBB to function as endcap does indeed increase the amount of organic Br in the product.

All of the yields reported in the preceding discussion are based on actual weight of isolated material after workup and are calculated as shown below based on the number of moles of resorcinol and dibromobenzene used. Those starting material amounts are used to calculate the amount of $K_2$-RC salt and KBr one would obtain theoretically. The theoretical yield is then based on mass balance, where the # moles of KBr=2×# moles of RC-salt, since the PDBB is used in excess.

Theoretical Mass=(wt $K_2$-RC salt+wt PDBB-wt KBr)

% Yield=Actual mass/theoretical mass×100%

The invention claimed is:
1. A method for preparing aryl ether oligomers, said method comprising reacting dihalobenzene with a salt of dihydroxybenzene,
   wherein the number of moles of dihalobenzene exceeds the number of moles of the salt of dihydroxybenzene; and
   wherein the ratio of the number of moles of dihalobenzene to the number of moles of the salt of dihydroxybenzene is from about 1.1:1 to about 1.9:1.
2. The method of claim 1 further comprising removing aryl compounds with one or two benzene rings from the reaction product produced by reacting dihalobenzene with a salt of dihydroxybenzene.
3. The method of claim 1, wherein dihalobenzene is reacted with the potassium salt of resorcinol.

TABLE 10

Effect of RC:PDBB Stoichiometry on Organic Bromine (oBr) Content[a]

| Example No. | RC:PDBB mol ratio | Cat. | Ligand[b] | Cat/L Mol %[c] | Measured oBr, % | Calculated oCl, %[d] | Calculated oI, %[d] |
|---|---|---|---|---|---|---|---|
| 93 | 1:1.00 | CuO | phen | 2/3 | 0.8 | 0.4 | 1.3 |
| 94 | 1:1.25 | CuO | phen | 2/3 | 9.6 | 4.3 | 15.2 |
| 95 | 1:1.50 | CuO | phen | 2/3 | 19.3 | 8.6 | 30.7 |
| 96[e] | 1:1.00 | CuO | phen | 2/3 | 0.5 | 0.2 | 0.8 |

[a]Reactions were run for 20 hr at reflux. Samples were worked up by shaking with dilute HCl and methylene chloride and stripping the organics to a residue.
[b]phen = 1,10-phenanthroline
[c]Mol % based on moles RC used.
[d]Estimated based on molecular weight differences between bromine, chlorine, and iodine.
[e]Reaction used 2.50 Equivalents of KOH.

4. The method of claim 3, wherein said dihalobenzene is 1,4-dibromobenzene and 1,4-dibromobenzene is reacted with the potassium salt of resorcinol in the presence of a copper containing catalyst.

5. The method of claim 4, wherein said copper containing catalyst is selected from the group consisting of cupric oxide and cupric salt.

6. The method of claim 5, wherein said cupric salt is cupric acetate.

7. The method of claim 3, wherein said potassium salt of resorcinol is prepared by the steps of:
(a) preparing a reaction mixture by combining said 1,4-dibromobenzene, said resorcinol, an aqueous solution KOH, and a solvent; and
(b) heating the reaction mixture of step (a) to reflux to remove water.

8. The method of claim 7, wherein the molar ratio of said 1,4-dibromobenzene to said resorcinol in step (a) is from about 1.1:1 to about 1.6:1; and
wherein the molar ratio of KOH to resorcinol is from about 1.8:1 to about 2.5:1.

9. The method according to claim 8, wherein the molar ratio of KOH to resorcinol is from about 2.1:1 to about 2.5:1.

10. The method of claim 9, further comprising the steps of:
(c) removing KBr salts from the product mixture of step (b) by filtration;
(d) stripping the solvent from the product mixture of step (c) to form an organic residue;
(e) washing the organic residue of step (d) with a dilute aqueous solution of a base followed by water washing; and
(f) removing residual 1,4-dibromobenzene from the washed organic residue of step (e) by distillation.

11. The method of claim 10, wherein a ligand is added with said copper containing catalyst to the reaction mixture of step (c).

12. The method of claim 11, wherein said ligand is selected from the group consisting of 1,10-phenanthroline, dimethylglycine, 1-butylimidazole, 1-methylimidazole and DL-alanine.

13. The method of claim 11, wherein the molar ratio of copper containing catalyst to resorcinol is from about 0.01:1 to about 0.04:1 and
wherein the molar ratio of copper containing catalyst to ligand is from about 1:3 to about 3:1.

* * * * *